US009427652B2

(12) United States Patent
Khademi

(10) Patent No.: US 9,427,652 B2
(45) Date of Patent: Aug. 30, 2016

(54) THERAPEUTIC DEVICE AND METHOD OF PROVIDING SPINAL SUPPORT

(76) Inventor: Ehsan Khademi, Chevy Chase, MD (US)

( * ) Notice: Subject to any disclaimer, the term of this patent is extended or adjusted under 35 U.S.C. 154(b) by 628 days.

(21) Appl. No.: 13/618,478

(22) Filed: Sep. 14, 2012

(65) Prior Publication Data

US 2013/0061856 A1 Mar. 14, 2013

Related U.S. Application Data

(60) Provisional application No. 61/534,415, filed on Sep. 14, 2011.

(51) Int. Cl.
| | | |
|---|---|---|
| *A47G 9/10* | (2006.01) | |
| *A61F 5/055* | (2006.01) | |
| *A47C 7/36* | (2006.01) | |
| *A63B 71/12* | (2006.01) | |
| *A61F 13/12* | (2006.01) | |
| *A61F 5/02* | (2006.01) | |
| *A47C 7/38* | (2006.01) | |
| *A47C 7/42* | (2006.01) | |
| *A47C 16/00* | (2006.01) | |

(52) U.S. Cl.
CPC ........... *A63B 71/1291* (2013.01); *A47C 7/383* (2013.01); *A47C 7/42* (2013.01); *A47G 9/1081* (2013.01); *A61F 5/028* (2013.01); *A61F 13/128* (2013.01); *A47C 16/00* (2013.01)

(58) Field of Classification Search
CPC ...... A61F 13/128; A61F 5/055; A61F 5/026; A61F 5/028; A47C 7/36; A47C 7/383; A47C 7/386; A47C 7/42; A47C 16/00; A47C 16/005; A63B 71/1291; A61G 15/12; Y10S 128/23; A47G 9/10; A47G 9/1081; A47G 9/109
USPC ....... 5/640, 636, 657, 652; 2/468, 207, 49.1, 2/111, 80, 75; 128/845–846
See application file for complete search history.

(56) References Cited

U.S. PATENT DOCUMENTS

| | | | | |
|---|---|---|---|---|
| 4,757,554 | A | * | 7/1988 | Blair ................................ 2/468 |
| 5,551,081 | A | * | 9/1996 | Starnes et al. .................... 2/468 |
| 5,738,640 | A | * | 4/1998 | Carlson-Orsi ................. 602/19 |
| 6,859,965 | B1 | * | 3/2005 | Gourd .............................. 5/646 |
| 2007/0094799 | A1 | * | 5/2007 | Wilson ............................. 5/639 |
| 2008/0251084 | A1 | * | 10/2008 | Marchetto ............... A61F 5/055 128/845 |

\* cited by examiner

*Primary Examiner* — Kari Petrik
(74) *Attorney, Agent, or Firm* — Franco S. DeLiguori; Bruce L. Adams

(57) ABSTRACT

A therapeutic device is configured to be worn by a user for providing spinal support to the user's body. The therapeutic device has a first support section and a second support section that connects to the first support section. The first support section is configured to comfortably engage and support the neck of the user's body. The second support section is configured to comfortably engage and support the lower back of the user's body while the first support section engages and supports the neck of the user's body to provide maximum support for an entire spinal region of the user's body with a level of comfort while maintaining a full range of motion for the user's spine.

11 Claims, 10 Drawing Sheets

THERAPEUTIC DEVICE AND METHOD OF PROVIDING SPINAL SUPPORT

CROSS-REFERENCE TO RELATED APPLICATIONS

The present Application for Patent claims priority benefit of Provisional Application No. 61/534,415 filed Sep. 14, 2011. This provisional patent application is hereby expressly incorporated by reference herein in its entirety.

BACKGROUND OF THE INVENTION

1. Field of the Invention

The present invention relates generally to the field of therapeutic devices, and more specifically to a therapeutic device in the form of a therapeutic pillow system that provides spinal support to assist users, such as travelers, commuters and athletes, in the prevention of neck and back related injuries, and that provides comfort to individuals with neck and back pain in a clinical setting under the supervision or recommendation of a doctor. The present invention also relates to a method of providing spinal support.

2. Background Information

It is well established that avid commuters and worldwide travelers often find themselves having to deal with the uncomfortable confines of public transportation such as planes, trains, buses and even some cars. It is also well established that a lack of proper neck and low back support when traveling, performing manual labor, daily tasks or participating in impact sports can contribute heavily to the development of neck and lower back problems.

While the preexisting knowledge of the need to maintain appropriate and sufficient support of the neck and lower back exists, often individuals are either uneducated or do not have the appropriate resources to obtain and use devices that assist in combating these all too common problems. There is also a lack of adequate information available to these individuals on how to combat their lower back and neck pain.

There are numerous neck pillow and back support devices on the market geared towards accommodating commuters and travelers so that they are able to sleep and/or rest conveniently while en route to their final destinations at a given time. However, these devices often fall short in that they are not successfully designed to assist in ridding individuals of lower back pain and even neck pain. Most devices on the market are too thin or lack sufficient padding to provide the essential comfort and support the neck and lower back truly needs to remain healthy and pain free. Such devices are also not ergonomically designed to conform to the natural curvature of the human spine while allowing for full range of motion of the entire spine. Additionally, such devices are one-dimensional and fail to provide the necessary support to be more versatile and benefit other consumers aside from the average traveler. Some of these other consumers include working individuals, athletes and routine sufferers of neck and lower back pain.

As a result of the foregoing problems with preventing lower back and neck pain and resulting injuries, a therapeutic device and a method of spinal support are desired that will aid in providing sufficient and comfortable support to the neck and back of a user while in a seated, laying down or standing position, while participating in sports activities, or while in a clinical setting under the supervision or recommendation of a doctor to provide comfort to the user with existing neck and back pain.

SUMMARY OF THE INVENTION

It is an object of the present invention to provide a therapeutic device that provides spinal support to assist in the prevention of neck and/or back related injuries.

It is another object of the present invention to provide a therapeutic device that provides spinal support for users during travel, at work, in public places or at home while in a seated, laying-down or standing position to prevent the development of neck and lower back pain.

It is another object of the present invention to provide a therapeutic device that provides spinal support for individuals participating in sports activities with risk of extreme impact, such as skiing, snowboarding or skateboarding, to protect such individuals from whiplash, spinal, and other related injuries.

It is another object of the present invention to provide a therapeutic device that provides comfort to individuals with neck and back pain in a clinical setting under the supervision or recommendation of a doctor.

It is a further object of the present invention to provide a therapeutic device that is configured to conform to the natural curvature of the user's spine in an efficient and effective manner.

It is still a further object of the present invention to provide a therapeutic device that is configured to be contracted to the comfort preferences of its users via the use of various securing means such as buckling clips, snap buttons or internal draw-cord system.

Yet another object of the present invention is to provide a therapeutic device that is configured to be worn by a user as a therapeutic jacket or vest for protection during performance of various contact and impact sports.

Yet another object of the present invention is to provide a therapeutic device that utilizes memory foam to provide adequate support and cushioning for its users.

Still another object of the present invention is to provide a therapeutic device that is comfortable for the user to use while allowing for a full range of motion of the entire spine of the user.

Still a further object of the present invention is to provide a method of spinal support.

The foregoing and other objects of the present invention are carried out by a therapeutic pillow system including a first pillow body having a midsection and a pair of end portions extending from opposite sides of the midsection, and a second pillow body having a pair of end portions connected to respective ones of the pair of end portions of the first pillow body to form a unitary therapeutic device configured to be worn on a user's body so that the first pillow body supports the neck of the body while the second pillow body supports the back of the body.

The therapeutic pillow system further includes a pair of strap members that interconnect respective ones of the pair of end portions of the second pillow body to respective ones of the pair of end portions of the first pillow body. A releasable securing assembly is provided for releasably securing the pair of strap members to one another to securely mount the therapeutic device on the user's body. An adjusting assembly is provided for adjusting the pair of strap members to position the therapeutic device relative to the user's body. According to one feature of the present invention, each of the first pillow body and the second pillow body comprises a fill material covered by a fabric cover. In a preferred embodiment, fill material comprises microfiber beads, and the fabric cover is fabricated from a soft pliable, breathable, anti-microbial material.

In one embodiment of the therapeutic pillow system, the first pillow body and the second pillow body are integrally connected to and non-releasable relative to one another. In another embodiment, the first pillow body and the second pillow body are separate and independent from and releasably connected to one another.

In another aspect, the present invention is directed to a therapeutic device configured to be worn by a wearer for providing spinal support to the wearer's body. The therapeutic device includes a first support section configured to comfortably engage and support the neck of the wearer's body, a second support section connected to the first support section and configured to comfortably engage and support the lower back of the wearer's body while the first support section engages and supports the neck of the wearer's body, and a securing assembly configured to releasably secure the first and second support sections to the wearer's body so that the first and second support sections simultaneously engage and support the neck and lower back, respectively, of the wearer's body.

In yet another aspect, the present invention is directed to method of spinal support by a therapeutic device that is worn by a user. The method comprises positioning a first support section of the therapeutic device relative to a neck region of the user's body, positioning a second support section of the therapeutic device relative to a lower back region of the user's body, and connecting and/or adjusting selected portions of the first and second support sections relative to one another and to the user's body so that the first and second support sections simultaneously support the neck and lower back, respectively, of the user's body to provide maximum support for an entire spinal region of the user's body with a level of comfort while maintaining a full range of motion for the user's spine.

BRIEF DESCRIPTION OF THE DRAWINGS

The foregoing summary, as well as the following detailed description of the preferred embodiments of this invention, will be better understood when read in conjunction with the accompanying drawings. In order to illustrate the invention, there is shown in the drawings embodiments which are presently preferred. However, it is understood that the invention is not limited to the precise arrangement and portions shown. In the drawings.

DETAILED DESCRIPTION OF THE INVENTION

Figure 1A:
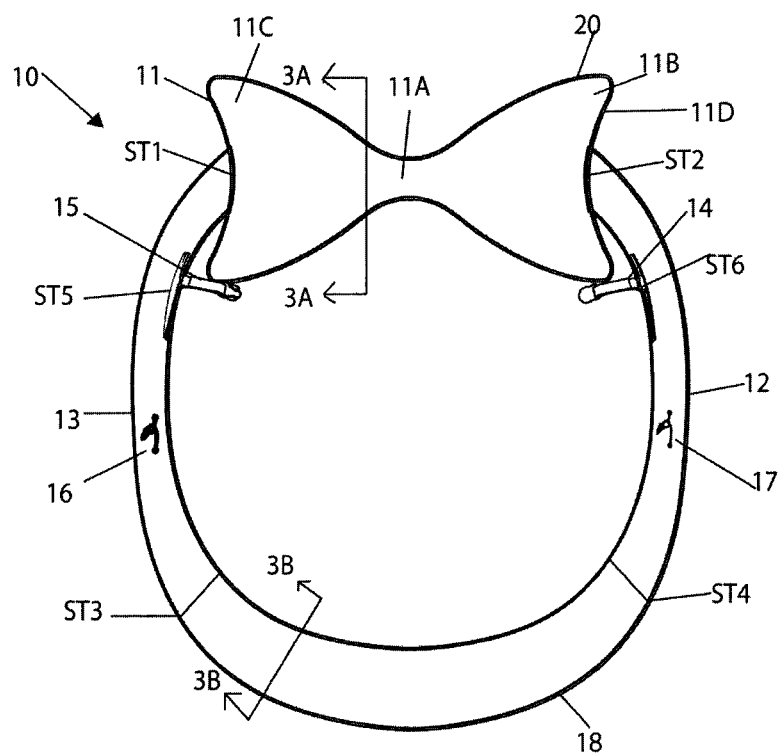
FIG. 1A is a front view of a therapeutic device in accordance with a first embodiment of the present invention.

While this invention is susceptible of embodiments in many different forms, this specification and the accompanying drawings disclose only presently preferred embodiments of the invention. The invention is not intended to be limited to the embodiments so described, and the scope of the invention will be pointed out in the appended claims.

Certain terminology is used in the following description for convenience only and is not intended to be limiting. The words right, left, front, top, rear, back, upper, lower, inner, outer, rearwardly and forwardly designate directions in the drawing to which reference is made. Such terminology includes the words above specifically mentioned and words of similar import.

The preferred embodiments of the therapeutic device according to the present invention are described below with specific application to certain features that assist in supporting the neck and back of the user's body while providing comfort to the user. Additionally, the therapeutic device is also suitable to provide comfort to other parts of the body such as the shoulder, arms and head.

The therapeutic device according to the present invention is described herein with a particular application for use by humans. It will be appreciated, however, that the therapeutic device of the present invention is also well-suited for use by animals, such as cats, dogs, and horses.

Referring now to the drawings in detail, wherein like numerals are used to indicate like elements throughout, there is shown in FIGS. 1A to 4B a therapeutic device, generally designated at 10, according to a first embodiment of the present invention. FIGS. 1A to 1D show front, rear and side views of the therapeutic device 10 in an open, unsecured state for the purpose of illustrating the various device components and corresponding interconnections, dimensional and positional relationships. FIGS. 2A to 2D are schematic views showing the therapeutic device 10 mounted on a user in a state in which the therapeutic device is not completely mounted and secured to a user's body (FIGS. 2A, 2D) and in a state in which the therapeutic device is completely mounted and secured to the user's body (FIGS. 2B, 2C, 2E).

Figure 1B:
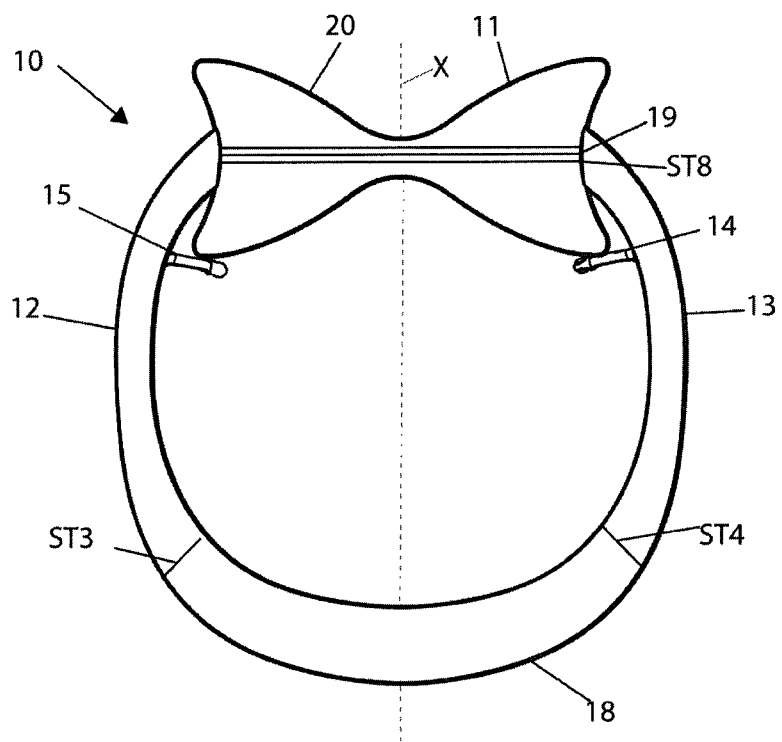
FIG. 1B is a rear view of the therapeutic device shown in FIG. 1A.
Figure 1C:
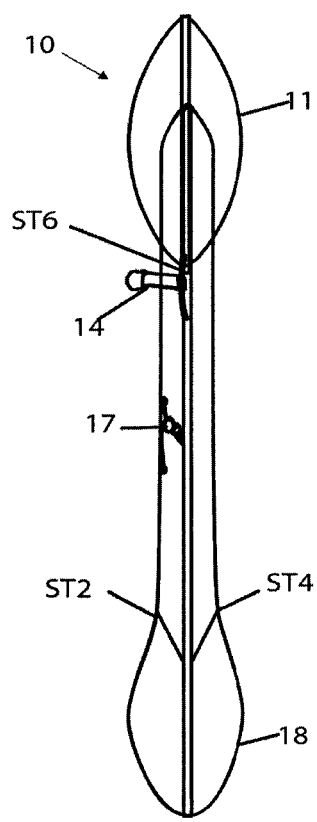
FIG. 1C is a side view of the therapeutic device shown in FIG. 1A.

Referring to FIGS. 1A-1C, the therapeutic device has a first support section 11 and a second support section 18. The first support section is generally bow-shaped with a narrow midsection 11A and widened side sections 20 having respective end portions 11B, 11C extending from opposite sides of the midsection 11A. The second support section 18 has a pair of end portions connected to respective ones of the pair of end sections 11B, 11C. A strap member 12 has one end connected at ST4 (e.g., via stitching) to one of the end portions of the second support section 18 and another end connected at ST2 (e.g., via stitching) to the end section 11D of the first support section 11. A strap member 13 has one end connected at ST3 (e.g., via stitching) to the other of the end portions of the second support section 18 and another end connected at ST1 (e.g., via stitching) to the end section 11C of the first support section 11. By this construction, the first and second support sections 11, 18 and the strap members 13, 14 form an integral, unitary structure (full and continuous version) such that the first and second support sections are non-releasable relative to one another.

A pair of releasable connectors or securing members 14, 15 are attached at ST6, ST5 (e.g., by stitching), respectively, to respective ones of the strap members 12, 13. By this construction, during use of the therapeutic device 10 as further described below with reference to FIGS. 2A-2E, the strap members 12, 13 are configured to comfortably engage the user's shoulders while permitting a full range of motion for the user's spine. In the present embodiment, the securing members 14, 15 are in the form of buckle-type connectors (e.g., buckle clips) and, as further described below, are configured to releasably secure the strap members 12, 13 to one another during use of the therapeutic device 10. When mounting the device 10 on the user's body, the connectors 14, 15 are buckled to achieve a firm fit and support of the device 10 on the user's body depending on the user's comfort level. When buckled, the connectors 14, 15 allow the first support portion 11 to conform to the neck area of the user as shown in FIGS. 2B and 2E. As such, the first support section 11 constitutes a neck support portion of the therapeutic device 10. In a modified embodiment of the therapeutic device 10 shown in FIG. 4B, the releasable securing members are in the form of snap buttons 21 attached to the strap members 12, 13. Alternative types of releasable securing members that can be used include, without limitation, hook and loop connection structures, ties, hooks and similar types of releasable securing members.

Figure 4A:
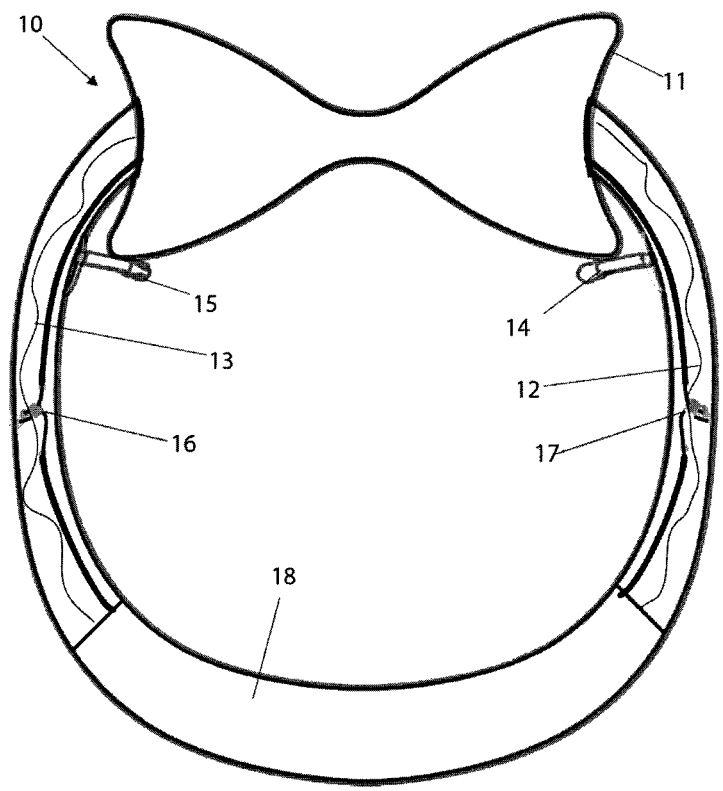
FIG. 4A is a partial cross-sectional view of the therapeutic device shown in FIG. 1A illustrating an adjusting assembly mounted in first and second strap members of the therapeutic device.
Figure 4B:
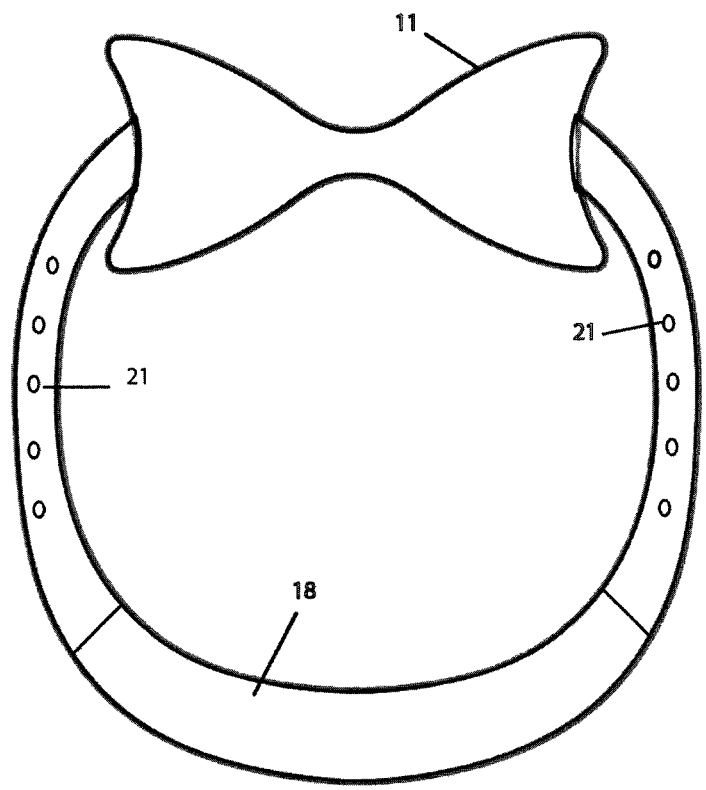
FIG. 4B is a front view of the modified form of the therapeutic device shown in FIG. 2C.

According to another feature of the present invention, an adjusting assembly is provided for adjusting the first and second strap members 12, 13 when mounting and positioning the therapeutic device 10 on and relative to the user's body as further described below with reference to FIGS. 2A-2E. Referring to FIGS. 1A, 1C and 4A, the adjusting assembly comprises a conventional draw-cord system including drawstrings 16, 17 mounted to (e.g., via stitching) and running internally in the strap members 12, 13, respectively, which is as best depicted in FIG. 4A showing the internal construction of the first and second strap members 12, 13 in partial cross-sectional view.

When mounting the therapeutic device 10 on a user's body, the drawstrings 16, 17 allow the user to adjust the device 10 relative to the body by pulling the drawstrings to bring the strap members 12, 13 towards one another. For example, by pulling tight on the drawstrings 16, 17, strap members 12, 13 are drawn inward toward the chest of the user for maximum support, as shown in FIG. 2B. Thus the drawstrings 16, 17 further supplement the support provided by the securing members 14, 15 in releasably securing the device 10 to the user's body by allowing the user to loosen and tighten the drawstrings depending on the conform level for the user. By the combined support and adjustment functions provided by the securing members 14, 15 and drawstrings 16, 17, the second support section 18 is allowed to conform to the lower back area of the user as shown in FIG. 2E. As such, the second support section 18 constitutes a lower back support portion of the therapeutic device 10.

By the foregoing construction of the therapeutic device 10 according to the present invention, the neck and lower back support portions 11, 18 provide first and second pillow bodies, respectively, configured to simultaneously firmly engage and comfortably support the user's neck and lower back, respectively, thereby resulting in a therapeutic pillow system providing effective spinal support to the user's body.

Figure 1D:
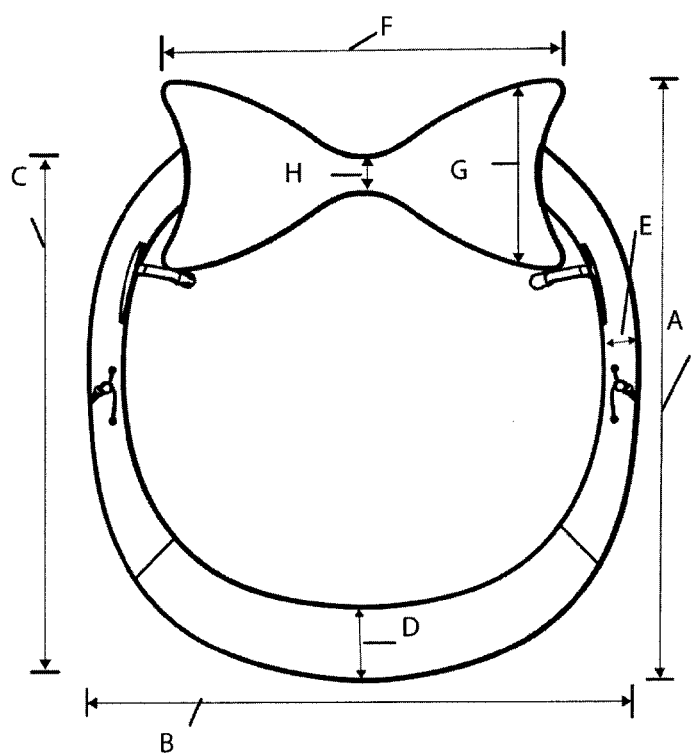
FIG. 1D is a front view of the therapeutic device according to the first embodiment illustrating relevant dimensions of portions of the therapeutic device.

It will be appreciated from the configuration shown in FIG. 1B that the therapeutic device 10 is substantially symmetrical about vertical axis X. Additionally, FIG. 1D shows various dimensions A-H of the therapeutic device 10. Preferably: A is in the range of about 350 mm to about 950 mm; B is in the range of about 200 mm to about 600 mm; C is in the range of about 300 mm to about 850 mm; D is in the range of about 30 mm to about 150 mm; E is in the range of about 10 mm to about 100 mm; F is in the range of about 300 mm to about 700 mm; G is in the range of about 50 mm to about 300 mm; and H is in the range of about 300 mm to about 150 mm. More preferably, A is about 825 mm, B is about 500 mm, C is about 725 mm, D is about 105 mm, E is about 50 mm, F is about 520 mm, G is about 240 mm, and H is about 75 mm.

Figure 3A:
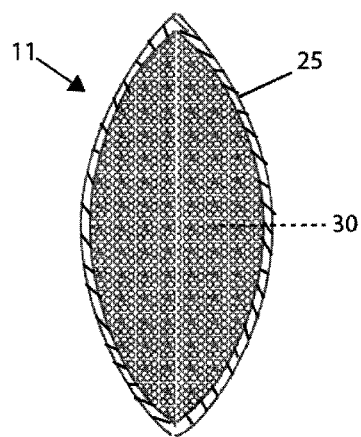
FIG. 3A is a cross-sectional view taken along line 3A-3A in FIG. 1A.
Figure 3B:
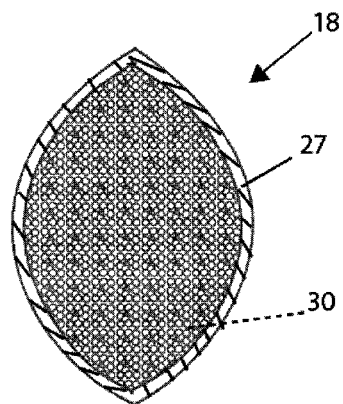
FIG. 3B is a cross-sectional view taken along line 3B-3B in FIG. 1A.

FIGS. 3A and 3B are cross-sectional views taken along lines 3A-3A and 3B-3B, respectively, in FIG. 1A. According to the present invention, the first and second support sections 11, 18 comprise a fill material 30 covered by respective fabric covers 25, 27 so that the first and second support sections 11, 18 form respective first and second pillow bodies. The fill material 30 may be stuffed inside the covers 25, 27 to provide sufficient firmness so that the first and second pillow bodies 11, 18 do not sag or droop when held while allowing the first and second pillow bodies to conform to the respective neck and lower back areas of the user's body. As shown in FIG. 1B, the first support section 11 may be provided with an opening providing access to the interior of the first support section via a zipper closure 19. The opening and zipper closure 19 will allow the user to selectively insert the filler material 30 into the interior of the support section 11 and to replace the same as necessary.

Preferably, the fill material 30 comprises beads made of microfiber, and the fabric covers 25, 27 are made of a durable and comfortable material, such as a soft pliable, breathable, anti-microbial fabric material, such as fleece. The fill material 30 provides cushion and comfort when the first and second support sections 11, 18 rest against the user's neck and back areas, respectively, as described above. The first and second strap members 12, 13 are preferably made of the same material used for the fabric covers 25, 27, however, the first and second strap members are not stuffed with the fill material 30 or any other type of fill material. It is understood that the fill material 30, fabric covers 25, 27 and first and second strap members are not limited to the foregoing types of materials. Examples of other types of fill materials that may be used include polyester fibers and the like. Likewise, the fabric covers 25, 27 and the first and second strap members 12, 13 may be made of any other type of fabric material, such as cotton, nylon, LYCRA, denim, polyester and the like.

Figure 2A:
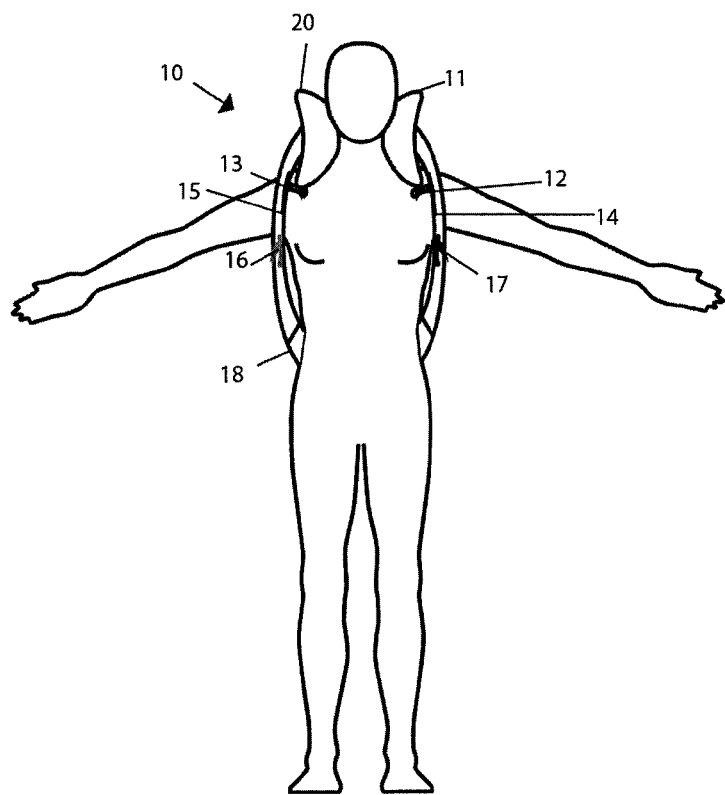
FIG. 2A is a schematic view illustrating the therapeutic device shown in FIG. 1A in a state in which the therapeutic device is not secured and completed mounted to a user's body.
Figure 2B:
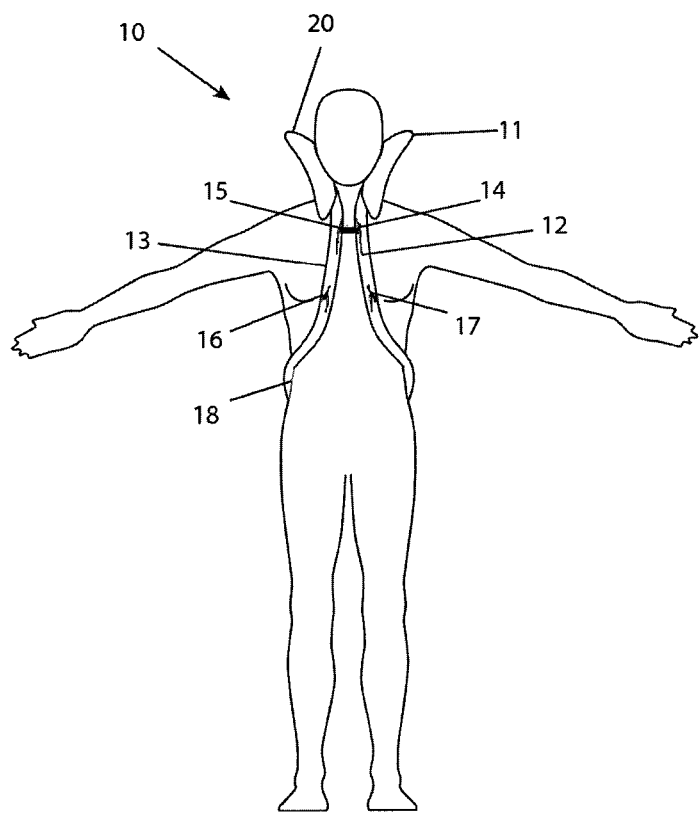
FIG. 2B is a schematic view illustrating the therapeutic device shown in FIG. 1A in a state in which the therapeutic device is secured and completely mounted to a user's body.
Figure 2C:
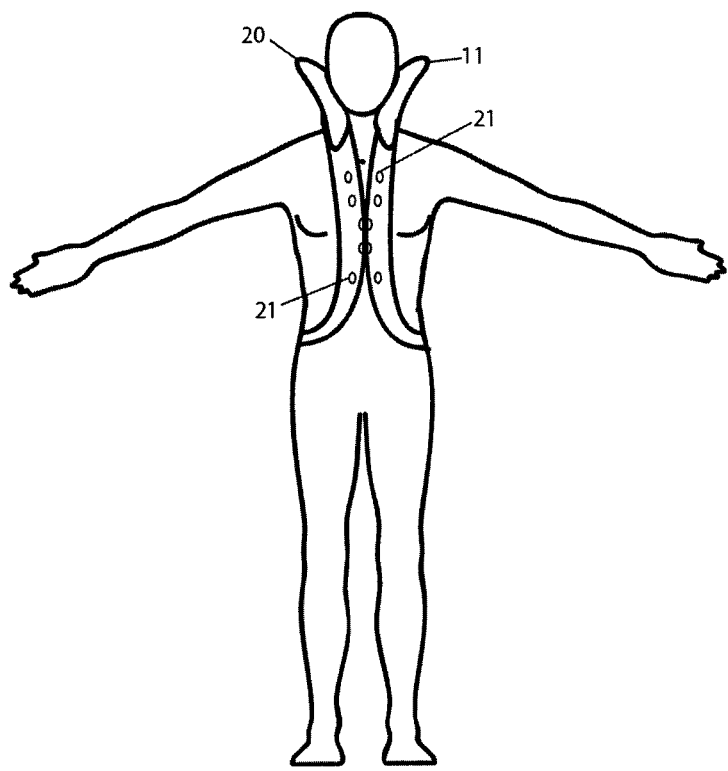
FIG. 2C is a schematic view illustrating a modified form of the therapeutic device shown in FIG. 1A while in a completely mounted and secured state relative to the user's body.
Figure 2D:
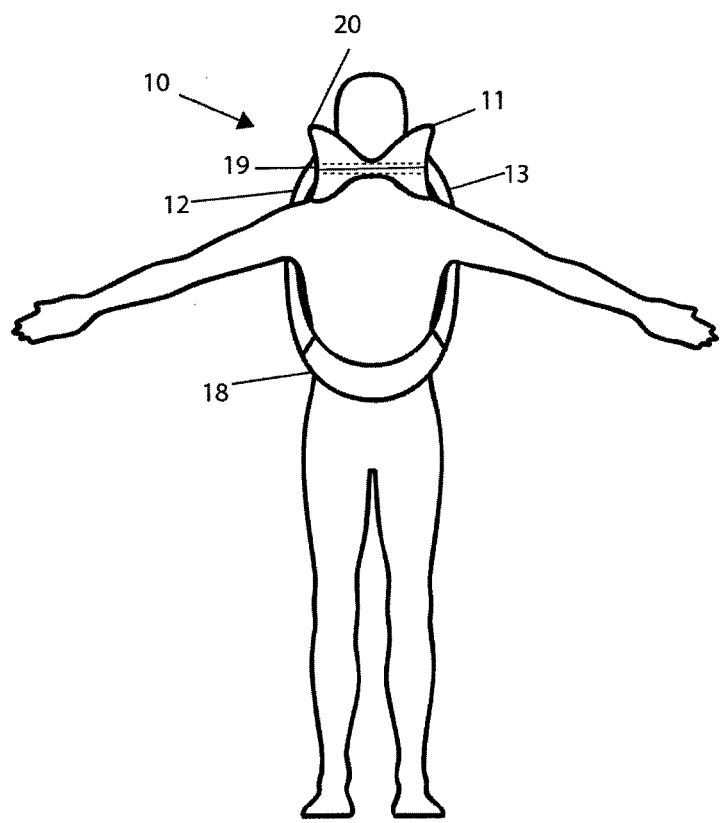
FIG. 2D is rear view of FIG. 2A.
Figure 2E:
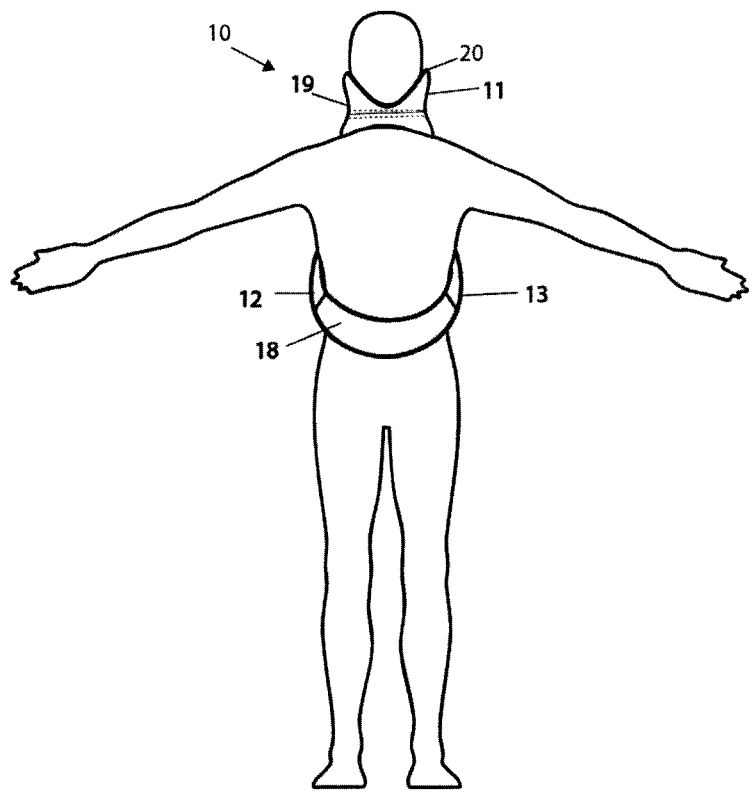
FIG. 2E is a rear view of FIG. 2B.

FIGS. 2A to 2E illustrate the manner of use of the therapeutic device 10 to provide spinal support to the user's body. FIGS. 2A and 2D are front and rear views, respectively, showing the therapeutic device 10 preliminarily and not yet fully mounted, adjusted and secured to the user's body using the securing members 14, 15 and the drawstrings 16, 17. The mounting of the device 10 is accomplished in a backpack-like fashion by inserting one of the user's arm through one of the first 12 or second 13 strap member (left or right strap member, respectively, as shown in FIG. 2D) depending on the user's preference and then inserting the other of the first and second strap members in front of the user's body so that the neck support portion 11 is positioned and conforms behind the neck and the lower back support portion 18 is positioned at the base of the lower back. In the configuration shown in FIGS. 2A and 2D, the strap members 12, 13 are placed over the user's left and right shoulders, respectively.

FIGS. 2B and 2E are front and rear views, respectively, showing the therapeutic device 10 completely mounted and secured to the user's body using the securing members 14, 15 and with the drawstrings 16, 17 in a drawn, adjusted state. From the state of the device 10 shown in FIGS. 2A and 2D, the device 10 is mounted, secured and adjusted relative to the user's body to achieve the appropriate level of support and comfort by securing the first and second strap members 12, 13 across the user's chest and downwards toward the user's stomach region for maximum support using the securing means 14, 15 and lightly drawing (e.g., to a degree corresponding to the comfort level of the user) drawstring 16, 17 for extra support. For the modified form of the therapeutic device 10 shown in FIG. 4B, the device 10 is mounted on the user's body using snap buttons 21, as shown in FIG. 2C.

By the foregoing construction of the therapeutic device 10 and method of support according to the present invention, it will be appreciated that the first support section 11 (neck support portion) provides adequate spinal support for the user by conforming to the back of the neck and wrapping around the front right and left side of the user's face, as shown in FIGS. 2B, 2C and 2E. The first and second strap members 12, 13 can also be adjusted at different points for maximum comfort and support. In this regard, the first and second strap members connect across the chest, stabilizing the neck and lower back areas. Furthermore, when secured (tightened) using the securing members 14, 15, the right and left sides of the bow-shape of the first support section 11 rest against the respective left and right side of the user's head, allowing for adequate support, so that the first support portion does not run the risk of slippage and non-functionality like many of the existing pillows on the market. The second support section 18 (lower back support portion) provides strong support of the lumbar region of the lower back and in conjunction with the first support section 11, when further adjusted (e.g., lightly drawn) using the drawstrings 16, 17, they function together as a therapeutic pillow system to provide maximum support for the entire spinal region of the user's body. It will also be appreciated that in the mounted configuration shown in FIGS. 2B, 2C and 2E, the therapeutic device 10 is configured in the form of a therapeutic jacket or vest worn by the user to provide spinal support to the user's body.

By the foregoing construction and operational modes, the therapeutic device 10 of the present allows users to effectively achieve comfort while traveling, performing sports or under the instruction and supervision of a doctor to maintain the appropriate support needed to prevent neck and lower back pain. Additionally, the construction and corresponding design and configuration of the therapeutic device 10 provide for many user-friendly options, such as various types of securing means (e.g., securing members 14, 15) and adjusting assembly (e.g., internal draw-cord system 16-17), that allow users to customize the feel and overall support level they need to achieve comfort. The construction of the device 10 also allows the natural curvature of the spine to remain intact while providing a level of comfort and without compromising the full range of motion of the spine, as particularly desired by travelers and commuters. Thus the therapeutic device 10 according to the present invention is particularly suitable for all types of individuals, most notably commuters, workers and everyday travelers, as well as individuals with a history of lower back and neck pain who desire a therapeutic device that will help rid them of pain and help them to avoid future pain. The therapeutic device 10 is also suitable as a medical device to assist in preventing neck and lower back pain from recurring, and can additionally serve as a protection device to preserve the neck and lower back during contact sports such as skiing, skateboarding and other activities involving impact. The therapeutic device 10 of the present invention is also adapted for use by individuals of various ages, shapes and sizes.

FIGS. 5-7B show a second embodiment of the therapeutic device according to the present invention, generally designated at 100, for providing spinal support to a wearer's body.

Figure 5:
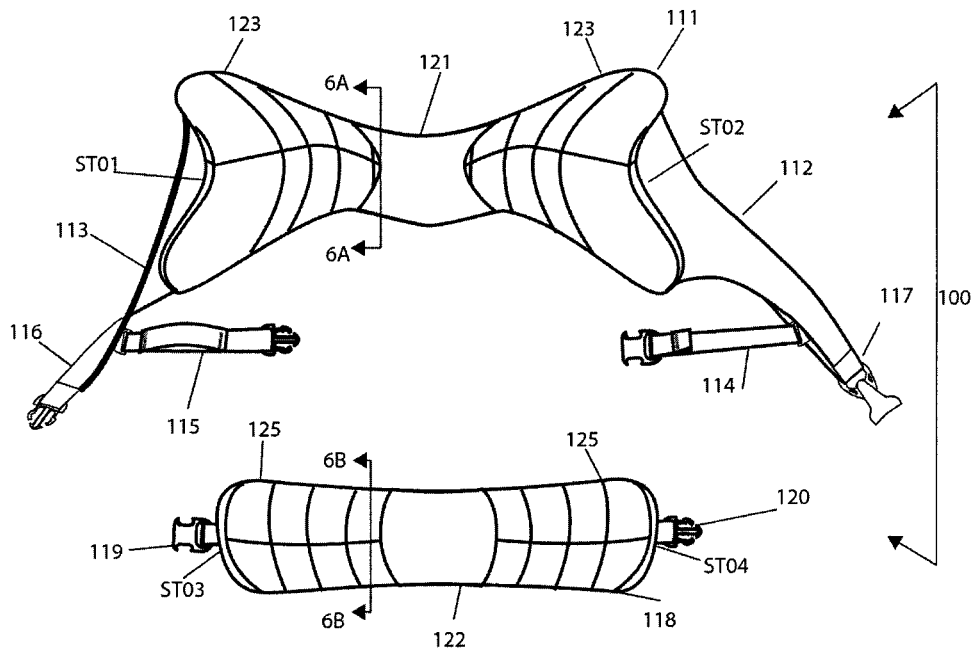
FIG. 5 is a front view of a therapeutic device in accordance with a second embodiment of the present invention.
Figure 7A:
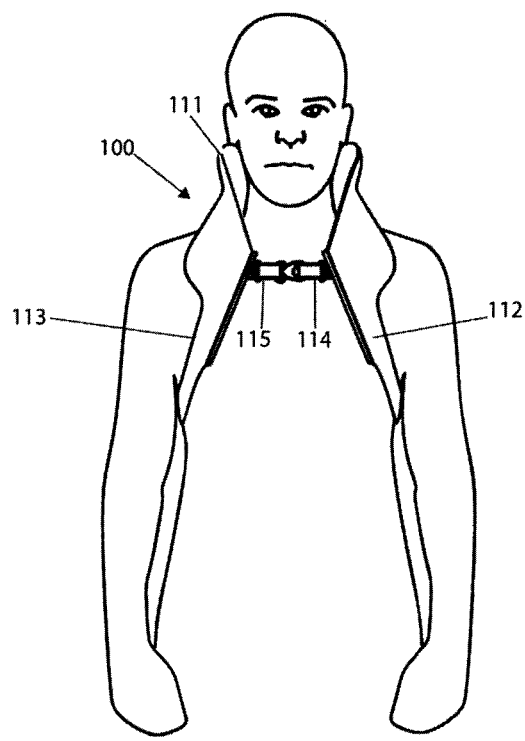
FIG. 7A is a schematic view illustrating the therapeutic device shown in FIG. 5 mounted on a user in a state in which the therapeutic device is completely mounted and secured to the user's body.
Figure 7B:
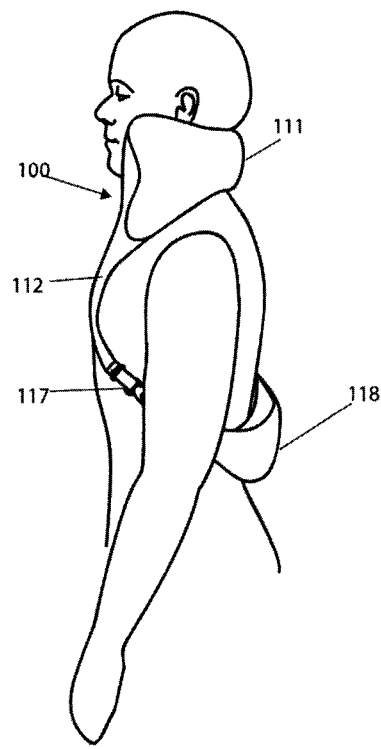
FIG. 7B is a side view of FIG. 7A.
Figure 7C:
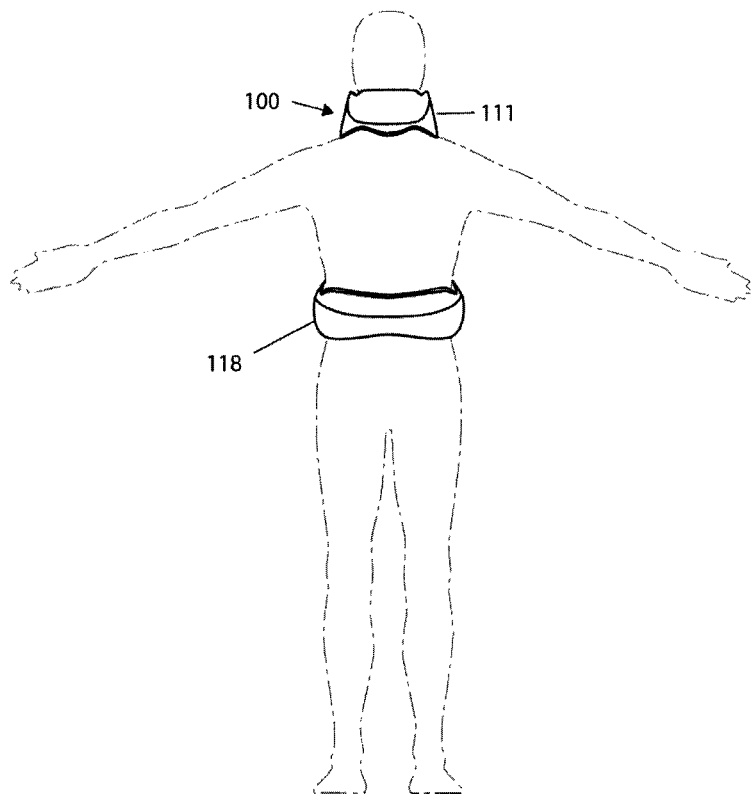
FIG. 7C is a rear view of FIG. 7A.

As shown in FIG. 5, the therapeutic device 100 comprises a first support section 111 (neck support portion) configured to comfortably engage and support the wearer's neck, a second support section 118 (lower back support portion) that releasably connects to the first support section 111 and is configured to comfortably engage and support the lower back of the wearer while the first support section 111 engages and supports the wearer's neck, and a releasable securing assembly (114-117 and 119-120) configured to releasably secure the first and second support sections 111, 118 to the wearer's body so that the first and second support sections simultaneously engage and support the neck and lower back, respectively, of the wearer's body, as shown in FIGS. 7A-7C.

The first support section 111 is generally bow-shaped with a narrow midsection 121 and widened side sections 123. The first support portion 111 is provided with extension pieces 112, 113 extending from and connected at regions ST02, ST01 (e.g., via stitching) to respective end portions of the widened side sections 123. The second support portion 118 is also bow-shaped, but to a lesser degree than the first support section 111, with a narrow midsection 122 and widened side sections 125. The releasable securing assembly comprises a plurality of releasable securing members or connectors, including first connectors 116, 117 provided at respective terminal end portions of the extension pieces 113, 112, second connectors 114, 115 connected to and extending from extension pieces 112, 113 at respective portions thereof located between the first connectors 116, 117 and regions ST01, ST02 at which the extension pieces are connected to the respective widened sections 123 of the first support section 111, and third connectors 119, 120 extending from and connected at regions ST03, ST04 (e.g., via stitching) to respective end portions of the widened sections 125 of the second support member 118.

As can be appreciated from FIG. 5, the therapeutic device 100 of the second embodiment differs from the therapeutic device 10 of the first embodiment in that the therapeutic device 100 does not have a unitary construction (i.e., with non-releasable first and second support sections) as described above for the therapeutic device 10. Instead, in the therapeutic device 100 the first support section 111 and the second support section 118 are structured separate and independent from one another and are configured for releasable connection to each other. More specifically, the first and second support sections 111, 118 are releasably connected to each other by releasable connection between the first connectors 116, 117 of the first support section 111 and the respective third connectors 119, 120 of the second support section 118, as shown in FIG. 7B. The second connectors 114, 115 of the first support section 111 are configured for releasable connection to one another as shown in FIG. 7A. In this embodiment, each of the connectors 114-117 and 119-120 of the releasable securing assembly comprises a buckle-type connector (e.g., buckle clip). However, it is understood that other types of releasable connectors may be used as described above for the first embodiment including, without limitation, snap buttons, hook and loop connection structures, ties, hooks and similar types of releasable securing members.

It can also be appreciated that the separate and independent construction of the first and second support sections 111, 118 permits these sections to be releasably connected together as shown in FIGS. 7A-7C and worn together by a user as a therapeutic pillow system or as a therapeutic jacket or vest. Alternatively, each of the first and second support sections 111, 118 may be used independently to support the neck and lower back region, respectively, of the user.

Figure 6A:
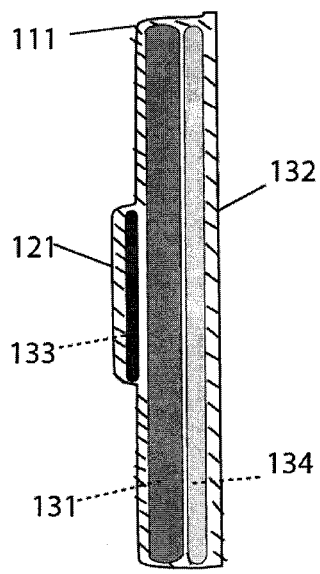
FIG. 6A is a cross sectional view taken along line 6A-6A in FIG. 5.
Figure 6B:
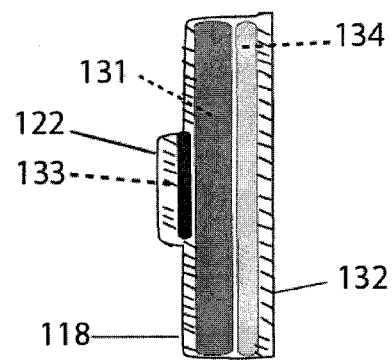
FIG. 6B is a cross sectional view taken along line 6B-6B in FIG. 5.

FIGS. 6A and 6B are cross-sectional views taken along lines 6A-6A and 6B-6B, respectively, in FIG. 5. As shown in FIGS. 6A, 6B, each of the first and second support sections 111, 118 is in the form of a pillow body comprising a multi-layer foam system (internal filling materials) covered by a fabric material (shell) 132. The fabric material 132 is preferably a durable, comfortable, stretchable fabric, such as spandex. The multi-layer foam system comprises a layer 134 of medium density EVA foam for imparting structure to the support section 111, a centrally located layer 131 of open cell PU foam for providing sufficient support on the back of the neck area, and a layer 133 as a spine member in the form of closed cell laytex memory foam. Preferably, the foam layers 131, 133 and 134 have thicknesses of about 25 mm, about 15 mm and about 10 mm, respectively. This construction of the multi-layer foam system provides outstanding support for the neck and lower back regions of the user, keeping the natural curvature of the human spine intact while allowing the user to still attain full range of motion in and around the spine while in a laying or sitting position.

Figure 6C:
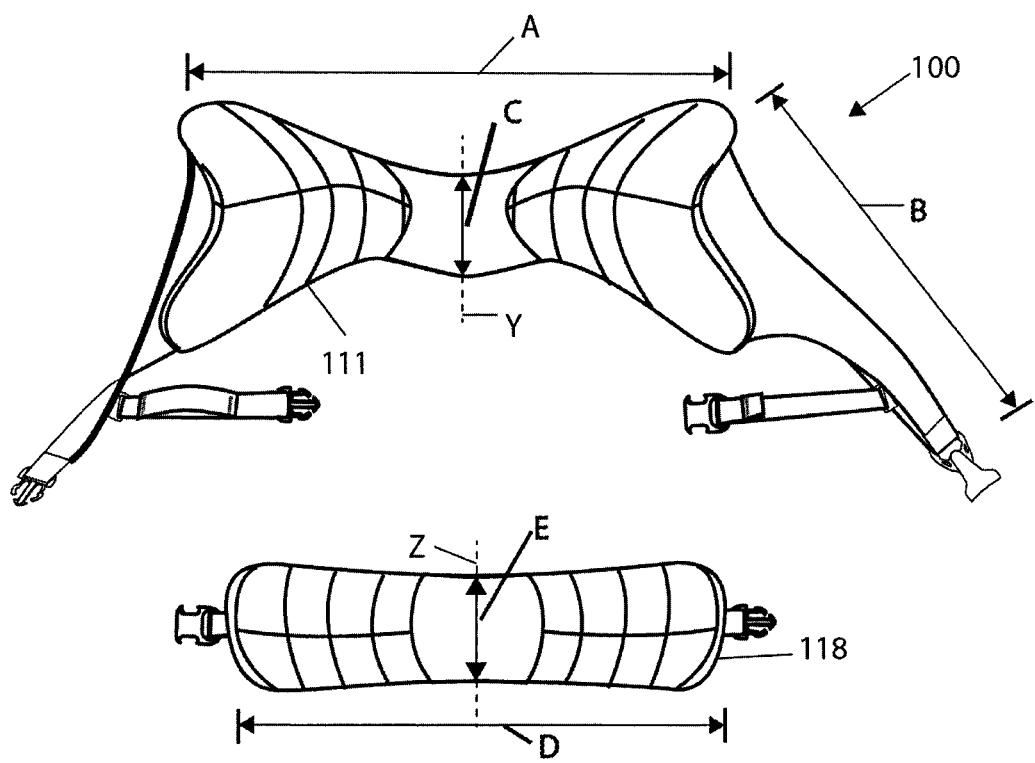
FIG. 6C is a front view of the therapeutic device according to the second embodiment shown in FIG. 5 illustrating relevant dimensions of portions of the therapeutic device.

It will be appreciated from the configuration shown in FIG. 6C that the first support section 111 is substantially symmetrical about vertical axis Y and that the second support section 118 is substantially symmetrical about vertical axis Z. FIG. 6C also shows various dimensions A-C and D-E of the first and second support sections 111, 118, respectively. Preferably: A is in the range of about 300 mm to about 700 mm, and more preferably about 400 mm; B is in the range of about 300 mm to about 700 mm, and more preferably about 500 mm; C is in the range of about 50 mm to about 300 mm, and more preferably about 200 mm; D is in the range of about 200 mm to 600 mm, and more preferably about 300 mm; and E is in the range of about 30 mm to about 150 mm, and more preferably about 105 mm.

FIG. 7A is a schematic front view of a user wearing the therapeutic device 100 in accordance with the second embodiment. In this view, the user is seen with the neck fully supported by the first support section 111 by releasably connecting (e.g., buckling) the second connectors 114, 115 to each other. The neck is secured on both the left and right sides by the first support section 111 and allows for range of motion of the user's spine, but is positioned to prevent the user from developing neck pain by awkwardly resting the neck sideways for an extended period of time.

FIG. 7B is a schematic side view of the user wearing the therapeutic device 100 in FIG. 7A. In this view, the user is seen with the therapeutic device 100 fully secured via the second connectors 114-115 of the first support section 111, as described above, and via the first connectors 116, 117 of the first support section 111 which are releasably connected to the third connectors 119, 120, respectively, of the second support section 118. By this construction and corresponding position relative to the body of the user, the therapeutic device 100 provides ample support of both the back and neck regions while still maintaining a full range of motion for the user's spine as well providing a level of comfort that is desired by all travelers, commuters and athletes using the therapeutic device.

FIG. 7C is a schematic rear view of the user wearing the therapeutic device 100 shown in FIG. 7A. This view illustrates how the neck and lower back regions of the user are fully supported by the first and second support sections 111, 118 in a mounted state of the therapeutic device 100.

To mount the therapeutic device 100 on a user, the first connectors 116, 117 are clipped to the respective third connectors 119, 120 under the corresponding arms of the user to unite (releasably connect) the first support section 111 to the second support section 118 so that the second support section 118 supports the lower back of the user, as shown in FIGS. 7B, 7C, by conforming to the base of the user's spine. The second connectors 114, 115 of the first support section 111 are then clipped in the front of the user's body and across the user's chest to provide adequate support for the user's neck, as shown in FIGS. 7A-7C. The neck is secured by the first support section 111 on both the left and right sides of the neck while allowing the user's spine to undergo a full range of motion, however, the first support section 111 is positioned relative to the neck so as to prevent the user from developing neck pain by awkwardly resting the neck sideways for an extended period of time.

By the foregoing construction of the therapeutic device 100 and method of spinal support according to the present invention, it will be appreciated that the first support section 111 (neck support portion) provides adequate support for the user by conforming to the back of the neck and wrapping around the front right and left sides of the user's face, as shown in FIGS. 7A-7C. The first and second strap members 111, 118 can also be adjusted at different points for maximum comfort and support. In this regard, the second connectors 114, 115 are clipped so as to extend across the user's chest, stabilizing the user's neck and lower back area. The second support section 118 (lower back support portion) provides strong support of the lumbar region of the lower back and in conjunction with the first support section 111, they function together as a therapeutic pillow system to provide maximum support for the entire spinal region of the user's body. It will also be appreciated that in the mounted configuration shown in FIGS. 7A-7C, the therapeutic device 100 is configured in the form of a therapeutic jacket or vest that is worn by the user to provide spinal support to the user's body.

By the foregoing construction and operational modes, the therapeutic device 100 of the present invention allows users to effectively achieve comfort while travelling, performing sports or under the instruction and supervision of a doctor to maintain the appropriate support needed to prevent neck and lower back pain. Additionally, the construction and corresponding design and configuration of the therapeutic device 100 provides for many user-friendly options, such as various types of securing means (e.g., clip members 114-117, 119-120), that allow users to customize the feel and overall support level they need to achieve comfort. The construction of the device 100 also allows the natural curvature of the spine to remain intact while providing a level of comfort and without compromising the full range of motion of the user's spine, as particularly desired by travelers and commuters. Thus the therapeutic device 100 according to the present invention is particularly suitable for all individuals, most notably commuters, workers and everyday travelers, as well as individuals with a history of low back and neck pain who desire a therapeutic device that will help rid them of pain and help them to avoid future pain. The therapeutic device 100 is also suitable as a medical device to assist in preventing neck and low back pain from recurring, and can additionally serve as a protection device to preserve the neck and lower back during contact sports such as skiing, skateboarding and other activities involving impact. The therapeutic device 100 of the present invention is also adapted for use by individuals of various ages, shapes and sizes.

It will be appreciated from the foregoing description that the therapeutic device according to the present invention is comfortable and user friendly with multiple applications, such as a full and continuous version (unitary construction of first and second support sections in therapeutic device 10 shown in FIGS. 1A-4B) and a convertible version (non-unitary, separate and independent construction of first and second support sections in therapeutic device 100 shown in FIGS. 5-7C), as well as a version that can be integrated into a therapeutic jacket or vest. All applications of the therapeutic device according to the present invention allow the user to customize the level of support they would like to receive whether it be neck only, low back only, and both neck and low back. The customization of support level can be attained through various levels of the securing and adjusting assemblies provided on the therapeutic device.

While the present invention has been described in terms of specific embodiments, it is to be understood that the invention is not limited to these disclosed embodiments. This invention may be embodied in many different forms and should not be construed as limited to the embodiments set forth herein; rather, these embodiments are provided by way of illustration only and so that this disclosure will be thorough, complete and will fully convey the full scope of the invention to those skilled in the art. Indeed, many modifications and other embodiments of the invention will come to mind of those skilled in the art to which this invention pertains, and which are intended to be and are covered by both this disclosure, the drawings and the claims.

I claim:

1. A therapeutic pillow system comprising:
    a first pillow body having a midsection and a pair of end portions extending from opposite sides of the midsection;
    a second pillow body having a pair of end portions connected to respective ones of the pair of end portions of the first pillow body to form a unitary therapeutic device configured to be worn on a user's body so that the first pillow body supports a neck of the body while the second pillow body supports a lower back of the body;
    a pair of strap members interconnecting respective ones of the pair of end portions of the second pillow body to respective ones of the pair of end portions of the first pillow body; and
    securing means for releasably securing the pair of strap members to one another to securely mount the therapeutic device on the user's body;
    wherein the first and second pillow bodies are spaced apart so that the second pillow body is configured to directly engage a lumbar region of the lower back;
    wherein the pair of strap members is connected to the first and second pillow bodies and is configured to comfortably engage the user's shoulders while permitting a full range of motion of the user's spine;
    wherein each of the first pillow body and the second pillow body comprises a fill material covered by a fabric cover; and
    wherein the first pillow body, the second pillow body and the pair of strap members form a continuous loop structure.

2. The therapeutic pillow system according to claim 1; further comprising an adjusting assembly for adjusting the pair of strap members to position the therapeutic device relative to the user's body.

3. The therapeutic pillow system according to claim 1; wherein the fill material comprises microfiber beads.

4. The therapeutic pillow system according to claim 1; wherein the fabric cover is fabricated from a soft pliable, breathable, anti-microbial material.

5. The therapeutic pillow system according to claim 1; wherein the first pillow body is generally bow-shaped.

6. The therapeutic pillow system according to claim 1; wherein the first pillow body is generally bow-shaped with a narrow midsection and widened side sections having respective end portions extending from opposite sides of the midsection.

7. The therapeutic pillow system according to claim 6; wherein the therapeutic pillow system is substantially symmetrical about an axis intersecting the narrow midsection of the first pillow body.

8. The therapeutic pillow system according to claim 6; wherein the therapeutic pillow system is substantially symmetrical about an axis intersecting the narrow midsection of the first pillow body and a central portion of the second pillow body.

9. The therapeutic pillow system according to claim 1; wherein each of the pair of strap members has a unitary construction, the pair of strap members directly connecting the first and second pillow bodies to one another.

10. The therapeutic pillow system according to claim 1; wherein the second pillow body is configured to directly engage the lumbar region of the lower back of the user's body while the first pillow body supports the neck of the user's body.

11. A therapeutic device configured to be worn by a wearer for providing spinal support to the wearer's body, the therapeutic device comprising:
    a first support section configured to comfortably engage and support a neck of the wearer's body;
    a second support section connected to the first support section and configured to comfortably engage and support a back of the wearer's body while the first support section engages and supports the neck of the wearer's body;

and a pair of securing members for releasably securing the first and second support sections to the wearer's body so that the first and second support sections simultaneously engage and support the neck and lower back, respectively, of the wearer's body;

wherein the first and second support sections are spaced apart so that the second support section is configured to directly engage a lumbar region of the lower back;

wherein each of the first support section and the second support section comprises a resilient fill material covered by a fabric cover;

and wherein the first support section is generally bow-shaped with a narrow midsection and widened side sections having respective end portions extending from opposite sides of the midsection; and wherein the therapeutic device is substantially symmetrical about an axis intersecting the narrow midsection of the first support section and a central portion of the second support section.

\* \* \* \* \*